United States Patent [19]

Auvil et al.

[11] Patent Number: 4,503,260

[45] Date of Patent: Mar. 5, 1985

[54] GLYCOLALDEHYDE PROCESS

[75] Inventors: Steven R. Auvil, Macungie, Pa.; Patrick L. Mills, Creve Coeur, Mo.

[73] Assignee: Monsanto Company, St. Louis, Mo.

[21] Appl. No.: 504,001

[22] Filed: Jun. 13, 1983

[51] Int. Cl.$^3$ .............................................. C07C 45/49
[52] U.S. Cl. ................................... 568/462; 568/420; 568/458
[58] Field of Search ............... 568/458, 462, 420, 862

[56] References Cited

U.S. PATENT DOCUMENTS

| 2,848,500 | 8/1958 | Funck | 568/492 |
|---|---|---|---|
| 2,943,701 | 7/1960 | Funck | 568/492 |
| 4,200,765 | 4/1980 | Goetz | 568/462 |
| 4,238,418 | 12/1980 | Weiss | 568/458 |
| 4,382,148 | 5/1983 | Drent | 568/462 |
| 4,405,814 | 9/1983 | Carroll | 568/458 |
| 4,405,821 | 9/1983 | Goetz | 568/462 |
| 4,414,421 | 11/1983 | Drent | 568/462 |

FOREIGN PATENT DOCUMENTS

| 0002908 | 5/1982 | European Pat. Off. | 568/462 |
|---|---|---|---|
| 0061791 | 10/1982 | European Pat. Off. | 568/462 |
| 0130948 | 8/1982 | Japan | 568/458 |
| 0140948 | 8/1982 | Japan | 568/458 |
| 7407544 | 12/1974 | Netherlands | 568/458 |

Primary Examiner—Werren B. Lone
Attorney, Agent, or Firm—Joseph D. Kennedy; James W. Williams, Jr.

[57] ABSTRACT

Hemi-formals are reacted with hydrogen and carbon monoxide in the presence of certain rhodium catalysts to form glycol aldehyde.

10 Claims, No Drawings

GLYCOLALDEHYDE PROCESS

This invention relates to improvements in the production of glycol aldehyde by a process which comprises the reaction of hemi-formals, (for example, of formula R'—O—CH$_2$—OH) carbon monoxide and hydrogen in a solvent system in the presence of rhodium catalysts having certain ligands associated therewith. Preferably the reaction is carried out in the presence of basic organic amine compositions which promote the formation of glycol aldehyde. In the above formula R' is an alkyl or cycloalkyl group.

BACKGROUND OF THE INVENTION

Glycol aldehyde is a well known compound and is a useful intermediate for the preparation of other valuable products. For example, ethylene glycol, a valuable end product, as well as an intermediate, can be prepared from glycol aldehyde by hydrogenation. Processes for the production of glycol aldehyde by the reaction of formaldehyde with carbon monoxide and hydrogen in the presence of certain rhodium catalysts are described in the co-pending application of Alwyn Spencer, Ser. No. 256,183, filed Apr. 21, 1981 and the co-pending application of W. Eamon Carroll et al Ser. No. 290,622, filed Aug. 5, 1981, both of which applications are assigned to the same assignee as the present application, and in U.S. Pat. No. 4,200,765, issued to Richard W. Goetz on Apr. 29, 1980. The present invention is an improvement over the processes described in the aforesaid applications, both of which describe the use of formaldehyde or paraformaldehyde as a reactant—in contrast to the use of hemi-formals as reactants in the present invention. By using a hemi-formal instead of formaldenyde or para-formaldehyde, a number of advantages are gained, namely, no water is generated in the reaction system, any formaldehyde which is generated or released in the course of the reaction is readily converted to a hemi-formal and used for further reaction in the process, and there is no significant loss of formaldehyde per se or as hemi-formal in the overall operation of the present process.

As to the aforementioned patent, it is not believed to be any more pertinent to the present invention than the aforesaid applications because the patent makes no mention of the use of hemi-formals in the preparation of glycol aldehyde. The formaldehyde reactants disclosed in the above patent are formaldehyde, paraformaldehyde, methylal (formal) having the formula CH$_2$(OCH$_3$)$_2$ and polyoxymethylene.

As noted above, ethylene glycol can be produced by a two step process in which glycol aldehyde is an intermediate which is then hydrogenated to form the glycol. U.K. Patent Application GB No. 2,070,002A published Sept. 3, 1981, discloses a method for making ethylene glycol in which a formaldehyde di-sec-alkyl acetal is reacted with CO and H$_2$ using a single component catalyst of cobalt carbonyl to form an ethylene glycol mono-sec alkyl ether which is then hydrolyzed with water using an acidic catalyst to form ethylene glycol. The acetal employed described as having the formula

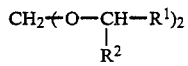

where R$^1$ and R$^2$ are each independently an alkyl group such as methyl, ethyl, propyl and butyl groups. Besides using an acetal which is different from hemi-formals employed in the present invention, the above application employs a cobalt-carbonyl catalyst which is quite different from the rhodium catalysts employed in the present invention.

SUMMARY OF THE INVENTION

The improved process of the present invention is carried out by reacting a hemi-formal (for example of formula R'—O—CH$_2$OH as described above), carbon monoxide and hydrogen in the presence of a rhodium catalyst having a modifying ligand in which at least one component is a tertiary organo phosphorous moeity or a tertiary organo arsenic moiety, under temperature and pressure conditions conducive to the formation of glycol aldehyde, the reaction being continued until such aldehyde is formed. Preferably, the reaction is carried out in the presence of a basic organic amine composition having a pKa value in excess of 1.0, more desirably a tertiary amine, such amine being used together with such catalyst during the reaction. Generally, the reaction is carried out at moderate, elevated temperatures and at elevated pressures and in a solvent, preferably a solvent which is also a solvent for the rhodium catalyst used.

DETAILED DESCRIPTION OF THE INVENTION

The rhodium catalyts used herein are comprised of a rhodium component in association with a modifying ligand having at least one of the components mentioned above and described in detail in U.S. Pat. No. 4,052,461, issued to Harold B. Tinker and Donald E. Morris on Oct. 4, 1977 and the aforementioned U.S. patent applications Ser. No. 256,183 and Ser. No. 290,622, both of which applications are hereby incorporated by reference in the present description. Other rhodium catalysts which may be employed in the present invention are rhodium catalysts used in the presence of a phosphine in which there is an electron withdrawing substituent on an aryl ring of the phosphine, for example, tris (4-trifluoromethylphenyl)phosphine. Such catalyts are described in greater detail in the co-pending application Ser. No. 409,819 of Albert S. Chan, filed Aug. 20, 1982, assigned to the same assignee as the present application, and which is hereby incorporated by reference in the present application. Generally, the rhodium component of the aforementioned catalysts is considered to be present in the form of a coordination compound. In addition to the rhodium component and modifying ligand, such coordination compound can include carbon monoxide (CO) ligands, hydride (H) ligands, halide or pseudohalide components, or various other ligands. The term "coordination compound" as used herein means a compound or complex formed by a combination of one or more electronically rich molecules or atoms capable of independent existence with one or more electronically poor molecules or atoms each of which may also be capable of independent existence. The rhodium may be complexed with from 3 to 6 or so ligands of which at least one is a modifying ligand as above mentioned, and can be in a form usually considered as neutral or essentially non-valent in common catalyst systems, or in cationic form as described in the aforesaid U.S. Pat. No. 4,052,461. The catalyst can be supplied to the reactants in active form or in the form of various catalyst precursors and the catalyst also may undergo changes in the course of the reaction, or from the effect of the reaction conditions.

The term "modifying ligand" used throughout this specification (as well as in aforesaid U.S. Pat. No. 4,052,461) means a tertiary organo phosphorus compound or a tertiary organo arsenic compound. Such compound is either coordinated to the rhodium atom to form the coordination compound or complex, or is present as the free compound, i.e., uncoordinated or uncomplexed or in both forms, in the reaction solution containing the rhodium coordination complex. In the free compound state such compound has the potential to become coordinated to the rhodium atom via a ligand exchange reaction with a different ligand already coordinated to the rhodium atom.

Suitable organo phosphorus and organo arsenic modifying ligands which may comprise part of the ionic or neutral rhodium coordination compound used in this invention are those containing trivalent phosphorus and/or trivalent arsenic atoms, and are referred to in this specification as phosphines or arsines.

In this group of suitable modifying ligands, the individual phosphorus or arsenic atoms have one available or unshared pair of electrons. An organic derivative of the phosphorus or arsenic with the foregoing electronic configuration is, therefore, a suitable ligand for the rhodium containing catalyst employed in this invention. Organic radicals of any size and composition may be bonded to the phosphorous or arsenic and the radicals are preferably selected from the group consisting of aryl and alkyl groups. The more preferred ligands are those consisting of at least one but preferably two or three aryl groups as the organic moieties. For example, preferred modifying ligands are illustrated by the following structural formulae $MR_3$ where M is P or As, and R is e.g. phenyl ($C_6H_5$—), or tolyl [($CH_3)C_6H_4$—], xylyl ($CH_3 \cdot C_6H_3 \cdot CH_3$—), e.g. $P(C_6H_5)_3$, $As(C_6H_5)_3$, $P[CH_3(C_6H_4)]_3$, $P(CH_3 \cdot C_6H_3)_3$, $P(CF_3 \cdot C_6H_4)_3$.

The more preferred group of modifying=° ligands includes the triaryl phosphines or triaryl arsines. The preferred component is the phenyl radicals or the substituted phenyl radical such as $CF_3 \cdot C_6H_4$.

The modifying ligands, and, if desired, other ligands, satisfy the coordination number of the central rhodium atom, and thus form a rhodium-containing complex. The term coordination compound or coordination complex means a compound or complex formed by combination of one or more electronically rich molecules or atoms, e.g. triphenylphosphine, carbon monoxide, 1,5-cyclooctadiene, (herein referred to as COD), with one or more electronically poor molecules or atoms, e.g. rhodium.

The rhodium complexes used in the present invention are ionic or neutral compounds, with the ionic ones having a non-complexing anionic moiety and the neutral ones containing halide, pseudohalide or hydride moiety. These have the general formula $RhL_xAn$. In this formula, in the case of the ionic ones, the rhodium moiety is $RhL_x$ and the non-coordinating anionic moiety $An^-$ is exemplified by $BF_4$, $PF_6$, $NO_3$, and $SiF_6 2$, and in the neutral ones An is halide, pseudohalide or hydride.

In the above formulae L is a ligand, (either the same or different ligands as described herein) and x varies from 2 to 5. The ligand L may or may not be a modifying ligand. For example, in the case where $[Rh(Ph_3P)_3]^+$ is employed as the rhodium-containing cation, $Ph_3P$ is the ligand L and it is also a modifying ligand. In the case where $[Rh(COD)(Ph_3P)_2]^+$ is employed as the rhodium-containing cation $Ph_3P$ and COD are the ligands L, but only $Ph_3P$ is a modifying ligand. Finally, in the case where $[Rh(COD)_2]^+$ is employed as the rhodium-containing cation, COD is the ligand L, and at least two moles of a modifying ligand such as $Ph_3P$ is furnished to the reaction solution per mole of rhodium to obtain the catalyst of the present invention. In cases where the ligand L is not a modifying ligand, then it is a ligand displaceable by carbon monoxide under reaction conditions, e.g., COD. Examples of the ligand L include:

mono-enes of 2 to 12 carbon atoms,
dienes of 4 to 12 carbon atoms,
trienes of 6 to 16 carbon atoms,
alkynes of 2 to 12 carbon atoms,
ketones of 3 to 12 carbon atoms,
nitriles of 2 to 12 carbon atoms,
N-alkylamines of 2 to 12 carbon atoms,
N-N-dialkylamides of 3 to 12 carbon atoms,
sulfoxides of 2 to 12 carbon atoms,
tertiary organo phosphorus compounds of 3 to 90 carbon atoms,
tertiary organo arsenic compounds of 3 to 90 carbon atoms,
tertiary organo antimony compounds of 3 to 90 carbon atoms,
carbon monoxide, and combinations thereof.

The ionic or neutral rhodium compounds described above are utilized in the present invention as a means of introducing rhodium into the reaction solution and are sometimes referred to as catalyst precursors. Other forms of rhodium may be used to form the rhodium catalyst, for example, rhodium metal or rhodium metal on carbon or rhodium halide may be introduced into the system to form the rhodium catalyst.

Although rhodium catalysts having not more than one modifying ligand associated with one rhodium atom are useful in the practice of this invention, it is preferred to employ an amount of phosphine or arsine compound in excess of one modifying ligand for each one rhodium atom. The reason for this preference is that a higher amount of modifying ligand has been found to provide a more stable and therefore reusable catalyst system than with lower amounts of modifying ligand. At the same time, the reaction rates and selectivity of rhodium catalysts containing such higher amounts of modifying ligand are quite satisfactory when using a basic amine composition in the process, whereas the reaction rates decrease considerably in the absence of basic organic amine compositions. Therefore, it is preferred to use the basic organic amine composition along with such rhodium catalyst. Amounts of phosphine or arsine compounds as high as 200 mols per rhodium atom in the catalyst complex have been used successfully in the present process, although some reduction in reaction rate and selectivity is experienced with such larger amounts.

The basic organic amine compositions employed in the hydroformylation process of this invention can be any amine compound, or combinations of compounds, which are basic in relation to any of the reactants or solvents employed in the process. The term "basic" is used herein to mean that the amine composition has a pH in water solution which is higher than the pH of such reactants or solvents.

As noted previously herein, the basic organic amines which can be used in the present process have a $pK_a$ of at least 1.0, which incidentally contrasts with the lower $pK_a$ values of N,N-disubstituted amides which usually have a pKa below 0.7. While amines having a $pK_a$ of at least 1.0 can be used, it is preferred to use amines having a $pK_a$ in the range of about 4.0 to about 12.5 since such amines generally provide improved reaction rates.

As examples of one class of basic organic amine compositions which can be used are basic amines having the structural formula

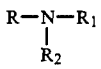

where R, $R_1$, and $R_2$ are the same or dissimilar organo radicals such as alkyl, aryl, alkaryl or aralkyl radicals or radicals of the foregoing kind which have been substituted with one or more substituents such as halide, hydroxyl, amine or other groups. Illustrative of such tertiary amines are trimethylamine, triethylamine, tributylamine, dimethylethylamine, triphenylamine, tributylamine, dimethylethyl amine, triphenylamine, triethanolamine, tri(chloromethyl)amine, 1,8-bis(dimethylamino)-napthalene, pyridine, polyvinylpyridine-styrene copolymers and the like.

It will be understood that the above listed compounds are merely illustrative and not limiting of the tertiary amine compounds, or combinations thereof, which are useful in the processes of this invention.

As further examples of basic organic amine compositions which can be employed are basic secondary amines having the structural formula

where R and $R_1$ have the same significance as stated above. Illustrative of such secondary amines are dimethylamine, diethylamine, dibutylamine, diphenylamine, diethanolamine, dichloromethylamine and the like. It will be understood that the above listed secondary amines are merely illustrative and not limiting of the secondary amine compounds, or combinations thereof, which are useful in the processes of this invention. Also, it is possible to use such secondary amines, or any of them, in combination with tertiary amines if desired.

As further examples of basic organic amine compositions which can be emloyed are basic primary amines having the structural formula:

where R has the same significance as stated above. Illustrative of such primary amines are monomethylamine, monoethylamine, monobutylamine, monophenylamine, mono(chloromethyl)amine, monoethanolamine and the like. It will be understood that the above listed compounds are merely illustrative and not limiting of the primary amines, or combinations thereof, which are useful in the processes of this invention. Moreover, it is possible to use such primary amines or any of them in combination with the hereinbefore described tertiary and/or secondary amines.

The hemi-formals employed in the processes of the present invention are, in general, the liquid reaction products of a primary or secondary monohydric alcohol and formaldehyde. The reaction products employed are liquids at temperatures above $-20°$ C. The preferred liquid reaction products are those of a $C_5$ to $C_{12}$ primary or secondary monohydric alcohol and formaldehyde, and have the generic formula $R'$—O—$CH_2$—OH, wherein $R'$ is an alkyl or cycloalkyl group having from 5 to 12, preferably from 5 to 10, carbon atoms. Such hemi-formals may be prepared by the processes disclosed in U.S. Pat. No. 2,848,500, dated Aug. 19, 1958 and U.S. Pat. No. 2,943,701,dated July 5, 1961, both granted to Dennis L. Funck, the disclosures of which patents are hereby incorporated in the present application by reference. As is disclosed in these patents, the hemi-formals derived from formaldehyde to which the patents are directed are generally liquid products at temperatures above $-15°$ C., and, as prepared for use in purifying formaldehyde, generally contain less than 1% of weight and preferably below 0.5% by weight of water. These hemi-formals also may contain an excess of formaldehyde over that required to react with the alcohol component of the hemi-formal, but, preferably, contain an excess of the alcohol component of the hemi-formal over that required to react with the formaldehyde. The preferred hemi-formal is liquid stoichiometric cyclohexyl hemi-formal or such hemi-formal containing an excess of cyclohexanol over that required to be combined with formaldehyde, which means that the formaldehyde content of the latter hemi-formal mixture will be in the range of about 20 to 22% as compared to 23.1% for 100% cyclohexyl hemi-formal. The water content of these preferred hemi-formal is less than 1% weight, and preferably less than 0.2% by weight.

The term hemi-formals as used herein is intended to include polymeric forms thereof such as those having the generic formulae $R'$—O—$(CH_2O)_n$—H and $R'$—O$(CH_2O)_m R'$, where $R'$ has the same significance as given above, n is 1-6 and m is 1-5. Thus, there is evidence that the liquid hemi-formals are composed of the monomeric as well as the polymeric forms and that the available ($CH_2O$) content is free to react with CO and $H_2$ to form glycol aldehyde. To illustrate, there is evidence that cyclohexy hemi-formal is present and utilized as cyclohexyl polyoxymethylene, i.e., $C_6J_{11}$—O—$(CH_2O)_n$—H, and bis-cyclohexyl ethers, i. e., $C_6H_{11}$—O$(CH_2O)_m C_6H_{11}$.

As is noted previously herein, there are certain advantages in using the hemi-formals in reaction with CO and hydrogen, which are not obtained by the use of formaldehyde, paraformaldehyde, or other HCHO precursors employed in prior art processes. Thus, one advantage is that no water is formed in the course of the reaction whereas water is formed when using, for example, paraformaldehyde. Therefore, since no water is formed, any formaldehyde in the glycolaldehyde reaction product is present as hemi-formal which can be recycled back to the process as a starting material, whereas when paraformaldehyde is used the glycol aldehyde reaction product containing water-formed in the reaction—and the unreacted formaldehyde either must be lost or separated from water by a relatively expensive procedure. In addition, when water is generated as when using HCHO or paraformaldehyde in the course of reaction, the unreacted formaldehyde is subject to loss due to condensation reactions either with itself or with the glycol aldehyde to form what are known as formose sugars. Additionally, the amide solvents and amine promoters which can be used in the reaction to form the glycol aldehyde, create a base reaction medium that promotes Cannizzaro-type reactions, for example, $$HCHO + HOCH_2(CHOH)_nCH_2OH + HCO_2^-,$$

and isomerization reactions by means of the Lobry de Bruyn-Alberda van Ekenstein rearrangement resulting in the formation of ketose (a rather undesirable end product) from aldose sugars. Such condensation reactions are obviated or substantially minimized using hemi-formals.

A third benefit is that the present process can be used in combination with a formaldehyde production plant to produce purified formaldehyde in the manner described in the aforementioned Funck patents and/or to form the hemi-formals used in the present process as reactants to produce glycol aldehyde. In either case, the formaldehyde produced is utilized in an economical manner and without significant loss.

The process of this invention can be practiced advantageously in any solvent which does not enter into reaction with the starting materials used, namely, the hemi-formals, carbon monoxide and/or hydrogen. Suitable solvents which may be used include the following: (1) nitriles, such as acetonitrile, benzonitrile, propionitrile, and the like; (2) cyclic ethers such as tetrahydrofuran, tetrahydropyran, dioxane, and the like; (3) ethers such as diethylether, alkyl ethers of alkylene glycols and polyalkylene glycols, for example, methyl ethers of ethylene glycol, methyl ethers of propylene glycol and methyl ethers of di-, tri-, and tetraethylene glycols, for example, tetraethylene glycol dimethyl ether (tetraglyme) and the like; (4) ketones, such as acetone, methyl isobutyl ketone, cyclohexanone and the like; (5) esters such as ethyl propionate, methyl laurate, ethyl acetate and the like. Another variety of suitable solvents is exemplified by N-substituted amides in which each hydrogen of the amido group is substituted by an organo group, usually a hydrocarbyl group such as an alkyl group as, for example, lower alkyl groups such as methyl, ethyl, propyl, butyl, hexyl, and the like. These amides are generally the amides of lower carboxylic acids, such as formic, acetic, propionic, hexanoic acids and the like. Specific amides of the above type which can be used include N, N-dimethylformamide, N,N-di-n-butylformamide, N,N-diisopentylformamide, N,N-dimethylacetamide, N,N-diethylacetamide, N-methyl-N-benzylformamide and the like. Other amides may also be used as solvents such as-methyl-pyrolidine-2-one, N-methyl piperidone, 1-benzyl pyrrolidine-2-one and the like.

As examples of other polar solvents which may be used are sulfoxides such as methyl sulfoxide, ethyl sulfoxide and the like, sulfones such as

in which R is methyl, ethyl or the like; phosphine oxides such as trimethylphosphine oxide, triethylphosphine oxide and the like; lactones such as propanolide, butanolide, and the like.

The above enumeration of solvents is illustrative and not intended to be limitative. In most instances, mixed solvents, that is, a homogeneous solution of two or more miscible solvents of the kind described above can also be used.

The preferred solvents for use in the present invention are acetone, acetonitrile, the N,N-alkyl substituted formamides and acetamides, such as those described above, and tetraglyme.

As noted herein, the present processes are usually carried out at moderately elevated temperatures and at elevated pressures. Generally, higher pressures provide the best reaction rates and selectivity, but pressures not in excess of 6000 psi (gauge) may be used if optimum reaction rates and selectivity are not required. The processes are temperature dependent and it is generally desirable to use moderate elevated temperatures of the order of 70° C. up to 150° C. and preferably from 90° C. up to 120° C.

The foregoing pressures are usually attained by the quantities of carbon monoxide (CO) and hydrogn (H$_2$) charged to the reaction zone or system, which is normally provided by an autoclave or other pressure resistant vessel. While the CO and H$_2$ react in a mole ratio of 1:1 in the present process, it is not necessary to have them present in such a ratio. The CO and H$_2$ may conveniently be used in a mole ratio of about 1:1 as available in synthesis gas, but can also be employed in widely varying ranges, such as CO:H$_2$ mole ratios varying from about 10:90 to about 90:10. Usually, however, it is desirable to employ CO:H$_2$ mole ratios in the range of about 4:1 to about 1:2, and to avoid large excesses of H$_2$ thereby suppressing methanol production. The CO and H$_2$ are usually employed in amounts sufficient to provide a pressure of from about 200 to about 5000 psig in the reaction zone at the temperatures employed. The preferred operating pressure during the primary reaction period is about 1500 to 4000 psig.

The amount of rhodium catalyst employed in the present processes does not appear to be critical and can vary considerably without adversely affecting the course of the reaction. In any event, the amount of catalyst used should be sufficient to catalyze the reaction of the hemi-formal, carbon monoxide and hydrogen to form glycol aldehyde. Also the amount used should be sufficient to achieve a reasonably practical reaction rate. Generally, the rhodium catalysts are used in amounts sufficient to provide at least about 0.001 gram atoms of rhodium, and up to about 0.09 gram atoms of rhodium, per liter of liquid reaction medium. The preferred amounts for most purposes are in the range of from about 0.003 to about 0.03 gram atoms per liter.

The organic amines, described above, can be used in widely varying amounts such as from less than 0.5 to more than 50 mols per rhodium atom, with a preference to use less of an amine as its basic character (pK$_a$ value) increases. With many of the more basic amines, for example, triethylamine, a range of about 1 to about 5 mols of amine per rhodium atom in the rhodium catalyst is preferred.

The following specific examples are intended to illustrate the processes of this invention, but not to limit the scope thereof. Parts and percentages are by weight unless otherwise specified.

EXAMPLE 1

A 300 milliliter stainless steel autoclave was used equipped with a magnedrive mechanical stirrer (supplied by Autoclave Engineers of Erie, Pa.), thermocouple, cooling coil, strain-gauge pressure transducer, temperature controller tachometer and sampling port. To this autolcave was charged 68.36 grs. of N,N-dimethylacetamide (solvent), 26.04 grs. (containing less than 0.1% water) of cyclohexyl hemi-formal, 0.1829 gr. of triethylamine, and the catalyst complex comprised of 0.345 gr. $RhCl(CO)[(C_6H_5)_3P]_2$ as catalyst precursor and 0.656 gr. of triphenylphosphine. The autoclave was sealed and flushed three times with CO to remove essentially all of the air. The autoclave was then pressurized to 40 psig with CO and the contents were heated to 100° C. with agitation, maintaining the stirrer speed at 1000 rpm.

When the temperature of the autoclave contents had become stabilized at about 100° C., the reactor pressure was rapidly adjusted to about 3000 psig using prelbended synthesis gas ($CO:H_2 = 1:1$ by volume) from a small gas reservoir maintained initially at about 4000 psig. The pressure in the autoclave was maintained substantially constant at about 3000 psig by a pressure regulator between the autoclave and reservoir. As the reaction proceeded, the pressure in the reservoir decreased. When the pressure approached the autolcave pressure (i.e., 3000 psig), the reservoir was charged with fresh synthesis gas of the same composition as originally used until the pressure in the reservoir reached about 4000 psig. Small (1 ml) samples were withdrawn from the autoclave through a bottom port connected to capillary tubing and an appropriate valving arrangement which had small dead-volume. Each sample was maintained in an ice bath and analyzed separately upon completion of the reaction by gas chromatography. A sample withdrawn after 15 minutes of reaction contained 3.66% formaldehyde, 0.21% water, 0.13% methanol, 2.26% glycol aldehyde, 17.68% cyclohexanol, 1,5.77% N-N-dimethylacetamide, 0.2% $C_3$ carbohydrates, 0.1% $C_4$ carbohydrates and 0.02% $C_5$ carbohydrates.

EXAMPLE 2

A reaction was carried out as in Example 1, except that the contents of the autoclave were heated at 110° C. and maintained at that temperature. A sample of the reaction product withdrawn after 15 minutes operation analyzed as follows: 1.97% HCHO, 0.18% $H_2O$, 0.12% $CH_3OH$, 4.27% glycol aldehyde, 20.1% cyclohexanol, 72.53% N,N-dimethylacetamide, 0.48% $C_3$ carbohydrates, 0.27% $C_4$ carbohydrates and 0.08% $C_5$ carbohydrates.

EXAMPLE 3

A reaction was carried out as described in Example 1, except that the contents of the autoclave were heated to 120° C. and maintained at that temperature. A sample of the reaction product withdrawn after 15 minutes of reaction analyzed as follows: 0.86% HCHO, 0.4% $H_2O$, 0.16% $CH_3OH$, 4.67% glycol aldehyde, 17.35% cyclohexanol, 74.98% N,N dimethylacetamide, 0.79% $C_3$ carbohydrates, 0.71% $C_4$ carbohydrates, and 0.08% $C_5$ carbohydrates.

EXAMPLE 4

The autoclave, equipped as described in Example 1, was charged with 73.36 grs. of N,N-dimethylacetamide, 26.4 grs. of cyclohexyl hemi-formal, 0.1821 gr. of triethylamine and 0.3455 gr. of $RhCl(CO)[C_6H_5)_3P]_2$ 0.3455 gr. of $RhCl(CO)[C_6H_5)_3P]_2$ providing a triphenylphosphine to rhodium molar ratio of 2. The same procedure was followed as in Example 1 except that the reaction temperature was 110° C. and the autoclave pressure was 2500 psig. A sample withdrawn after 15 minutes of reaction analyzed as follows: 4.03% HCHO, 0.27% $H_2O$, 0.1% $CH_3OH$, 1.16% glycol aldehyde, 19.44% cyclohexanol, 74.48% N,N-dimethylacetamide, 0.31% $C_3$ carbohydrates and 0.21% $C_7$ carbohydrates.

EXAMPLE 5

A reaction was carried out as described in Example 4 except that 1.574 grs. of triphenyl phosphine were added in addition to that contained in the rhodium catalyst precursor to provide a final triphenylphosphine to rhodium molar ratio of 14. A sample withdrawn after 20 minutes of reaction analyzed as follows: 1.86% HCHO, 0.39% $H_2O$, 0.18% $CH_3OH$, 2.37% glycol aldehyde, 19.53% cyclohexanol, 74.30% N,N-dimethylacetamide, 0.8% $C_3$ carbohydrates, and 0.57% $C_4$ carbohydrates.

EXAMPLE 6

A reaction was carried out as described in Example 4 except that 6.29 grs. of triphenylphosphine were added in addition to that contained in the rhodium catalyst precursor to provide a final triphenylphosphine to rhodium molar ratio of 50. A sample withdrawn after 20 minutes of reaction analyzed as follows: 1.9% HCHO, 0.41% $H_2O$, 0.13% $CH_3 OH$, 2.95% glycol aldehyde, 19.55% cyclohexanol, 72.65% N,N-dimethylacetamide, 1.0% $C_3$ carbohydrates, 1.27% $C_4$ carbohydrates, 0.12% $C_5$ carbohydrates, and 0.02% $C_6$ carbohydrates.

EXAMPLE 7

A reaction was carried out as described in Example 1 except that 0.069 of $RhCl(CO)[(C_6H_5)_3P]_2$ catalyst precursor was used and the reaction temperature was 110° C. A sample was withdrawn after 20 minutes and analyzed as follows: 5.08% HCHO, 0.18% $H_2O$, 0.092% $CH_3OH$, 0.49% glycol aldehyde, 21.3% cyclohexanol, 72.633% N,N-dimethylacetamide, 0.155% $C_3$ carbohydrates, and 0.07% $C_4$ carbohydrates.

In some of the examples which follow the results obtained by using hemi-formals are compared with the results obtained using paraformaldehyde as the formaldehyde source under substantially identical conditions. Thus, in Examples 8 and 9, also 10 and 11, and 12 and 13 these comparisons are made.

EXAMPLE 8

In this run the autoclave and its accessories, as described in Example 1 was used and the autoclave was pressurized with preblended synthesis gas ($CO:H_2=1:1$) all as described in Example 1, with the exception that the temperature of the autoclave contents was 110° C. The autoclave was charged with 81.03 grs. (86.48 $Cm^3$) of N,N-dimethylacetamide, 13.2 grs. (13.52 $cm^3$) of cyclohexanol hemi-formal, 0.1821 gr. of triethylamine, 0.345 gr. of $RhCl(CO)[(C_6H_5)_3P]_2$ catalyst precursor, and 0.656 gr. of excess triphenylphosphine, and these were reacted with CO and $H_2$. At a temperature of 110° C. the hemi-formal used provided an initial formaldehyde concentration (calculated as HCHO) of 1 gram mol per liter of the N,N-dimethylacetamide and hemi-formal. A sample of reaction product withdrawn from the autoclave after 15 minutes of reaction analyzed as follows: 1.18% HCHO, 0.53% $H_2O$, 0.085% $CH_3OH$, 1.69% glycol aldehyde, 9.70% cyclohexanol, 86.425% N,N-dimethylacetamide, 0.25% $C_3$ carbohydrates, 0.12% $C_4$ carbohydrates, and 0.02% $C_6$ carbohydrates. The formaldehyde conversion was 52.5% and the selectivity to glycol aldehyde was 59.6%.

EXAMPLE 9

The reaction was carried out as described in Example 8 except that the reactor was charged with 164 grs (175 cm$^3$) of N,N-dimethylacetamide, 5.152 grs. of paraformaldehyde (97% HCHO), 0.3221 gr. of triethylamine, 0.6046 gr. of Rh Cl (CO) [(C$_6$H$_5$)$_3$P]$_2$ catalyst precursor and 1.6065 gr. of excess triphenylphosphine. The paraformaldehyde used provided an initial formaldehyde concentration (calculated as HCHO) of 1 gram mol per liter of N,N-dimethylacetamide. A sample of reaction product withdrawn from the autoclave after 15 minutes of reaction analyzed as follows: 2.1% HCHO, 0.25% H$_2$O, 0.033% CH$_3$OH, 0.89% glycol aldehyde, 96.691% N,N-dimethylacetamide, 0.01% C$_3$ carbohydrates, 0.02% C$_4$ carbohydrates and 0.006% C$_5$ carbohydrates. The formaldehyde conversion was 30.1%.

EXAMPLE 10

The reaction was carried out as described in Example 8 except that the autoclave was charged with 74.7 grs. (79.72 cm$^3$) of N,N-dimethylacetamide and 19.53 grs. 8 cm$^3$) of cyclohexyl hemi-formal, providing an initial formaldehyde concentration (calculated as HCHO) of 1.5 gram mol per liter of N,N-dimethylacetamide plus cyclohexyl hemi-formal. A sample of reaction product withdrawn from the autoclave after 10 minutes of reaction analyzed as follows: 2.37% HCHO, 0.47% H$_2$O, 0.11% CH$_3$OH, 2.67% glycol-aldehyde, 14.97% cyclohexanol, 79.02% N,N-dimethylacetamide, 0.25% C$_3$ carbohydrates, and 0.14% C$_4$ carbohydrates. The formaldehyde conversion was 42.7% and the glycol aldehyde selectivity was 72.4%.

EXAMPLE 11

The reaction was carried out as described in Example 8 except that the autoclave was charged with 164 grs. (175 cm$^3$) of N,N-dimethylacetamide, 7.727 grs of paraformaldehyde (97% formaldehyde), 0.3261 gr. of triethylamine, 0.6046 gr. of RhCl (CO) [(C$_6$H$_5$)$_3$P]$_2$ catalyst precursor and 1.6065 grs. of excess triphenylphosphine. The paraformaldehyde used provided an initial formaldehyde concentration (calculated as HCHO) of 1.426 gram mol per liter of N,N-dimethylacetamide. A sample of reaction product withdrawn from the autoclave after 10 minutes of reaction analyzed as follows: 2.45% HCHO, 0.23% H$_2$O, 0.03% CH$_3$OH, 2.31% glycolaldehyde, 94.893% N,N-dimethylacetamide, 0.055% C$_3$ carbohydrates and 0.032% C$_4$ carbohydrates. The formaldehyde conversion was 44.5% and the glycol aldehyde selectivity was 58.1%.

EXAMPLE 12

The reaction was carried out as described in Example 8 except that the autoclave was charged with 55.7 grs (59.45 cm$^3$) of N,N-dimethylacetamide, 39.06 grs. (40.56 cm$^3$) of cyclohexyl hemi-formal, 0.1821 gr of triethylamine, 0.345 gr of RhCl(CO) [(C$_6$H$_5$)$_3$P]$_2$ catalyst precursor, and 0.656 gr of excess triphenylphosphine. The hemi-formal provided an initial formaldehyde concentration (calculated as HCHO) of 3 gram mol per liter of N,N-dimethylacetamide plus cyclohexyl hemi-formal. A sample of reaction product withdrawn from the autoclave after 10 minutes of reaction analyzed as follows: 5.07% HCHO, 0.44% H$_2$O, 0.13% CH$_3$OH, 4.82% glycol aldehyde, 32.09% cyclohexanol, 55.275% N,N-dimethylacetamide, 1.47% C$_3$ carbohydrates, 0.64% C$_4$ carbohydrates, and 0.064% C$_5$ carbohydrates. The formaldehyde conversion was 39% and the glycol aldehyde selectivity was 71.2%.

EXAMPLE 13

The reaction was carried out as described in Example 8 except that the autoclave was charged with 164 grs. (175 cm$^3$) of N,N-dimethylacetamide, 15.454 grs. of paraformaldehyde (97% formaldehyde), 0.3218 gr. of triethylamine, 0.6046 gr of RhCl(CO)[C$_6$H$_5$)$_3$P]$_2$ catalyst precursor, and 1.6065 grs. of exces triphenylphosphine. The paraformaldehyde provided an initial formaldehyde concentration (calculated as HCHO) of 2.853 gram mol per liter of N,N-dimethylacetamide. A sample of the reaction product withdrawn from the autoclave after 10 minutes of reaction analyzed as follows: 5.85% HCHO, 0.45% H$_2$O, 0.06% CH$_3$OH, 3.16% glycol aldehyde, 90.30% N,N-dimethyl-acetamide, 0.099% C$_3$ carbohydrates, 0.047% C$_4$ carbohydrates, 0.008% C$_6$ carbohydrates and 0.008% C$_7$ carbohydrates. The formaldehyde conversion was 30.5% and the glycol aldehyde selectivity was 60.2%.

A comparison of Examples 8, 10 and 12, indicates that as the hemi-formal concentration (and thereby the formaldehyde concentration) is increased the formaldehyde conversion decreases and the glycol aldehyde selectivity increases.

A comparison of Examples 8, 10 and 12 (wherein a hemi-formal was used) with Examples 9, 11 and 13, (wherein paraformaldehyde was used) respectively, is of interest in that substantially equal concentrations of formaldehyde from each source were employed. On the other hand, a comparison of Example 10 with Example 11 and of Example 12 with Example 13 showed that a hemi-formal gave both a higher formaldehyde conversion and glycolaldehyde selectivity than paraformaldehyde.

The following examples illustrate the effect of different CO:H$_2$ volume ratios on formaldehyde conversion and glycol aldehyde selectivity when a hemi-formal is employed in the reaction.

EXAMPLE 14

A reaction was carried out as described in Example 1 except that the preblended synthesis gas contained CO and H$_2$ in a volume ratio of 1:2, and the reaction temperature used was 110° C. A sample of the reaction product withdrawn from the autoclave after 20 minutes of reaction analyzed as follows: 1.62% HCHO, 0.43% H$_2$O, 0.35% CH$_3$OH, 4.45% glycol aldehyde, 20.5% cyclohexanol, 70.43% N,N-dimethylacetamide, 1.21% C$_3$ carbohydrates, 0.86% C$_4$ carbohydrates, and 0.08% C$_5$ carbohydrates. The formaldehyde conversion was 71.6% and the glycol aldehyde selectivity was 49.4%.

EXAMPLE 15

A reaction was carried out as described in Example 14 except that the preblended synthesis gas contained CO and H$_2$ in a volume ratio of 1:4. A sample of the reaction product withdrawn from the autoclave after 20 minutes of reaction analyzed as follows: 1.52% HCHO, 0.83% H$_2$O, 0.22% CH$_3$OH, 5.31% glycol aldehyde, 20.67% cyclohexanol, 69.61% N,N-dimethylacetamide, 0.89% C$_3$ carbohydrates, 0.85% C$_4$ carbohydrates, 0.08% C$_5$ carbohydrates, and 0.02% C$_6$ carbohydrates. The formaldehyde conversion was 70.3% and the glycol aldehyde selectivity was 66%.

EXAMPLE 16

A reaction was carried out as described in Example 14 except that the preblended synthesis gas contained CO and $H_2$ in a volume ratio of 1:9. A sample of the reaction product withdrawn from the autoclave after 20 minutes of reaction analyzed as follows: 1.77% HCHO, 0.4% $H_2O$, 0.3% $CH_3OH$, 4.64% glycol aldehyde, 20.8% cyclohexanol, 70.2% N,N-dimethylacetamide, 1.04% $C_3$ carbohydrates, 0.77% $C_4$ carbohydrates, and 0.08% $C_5$ carbohydrates. The formaldehyde conversion was 67.6% and the glycol aldehyde selectivity was 56.4%.

EXAMPLE 17

A reaction was carried out as described in Example 14 except that the preblended synthesis gas contained CO and $H_2$ in a volume ratio of 2:1. A sample of the reaction product withdrawn from the autoclave after 20 minutes of reaction analyzed as follows: 2.21% HCHO, 0.5% $H_2O$, 0.16% $CH_3OH$, 3.9% glycol aldehyde, 20.99% cyclohexanol, 71.24% N,N-dimethylacetamide, 0.62% $C_3$ carbohydrates, 0.31% $C_4$ carbohydrates and 0.07% $C_5$ carbohydrates. The formaldehyde conversion was 59.1% and the glycol aldehyde selectivity was 54.2%

EXAMPLE 18

A reaction was carried out as described in Example 14 except that the preblended synthesis gas contained CO and $H_2$ in a volume ratio of 4:1. A sample of reaction product withdrawn from the autoclave after 20 minutes of reaction analyzed as follows: 3.81% HCHO, 0.49% $H_2O$, 0.13% $CH_3OH$, 2.91% glycolaldehyde, 20.87% cyclohexanol, 71.02% N,N-dimethylacetamide, 0.44% $C_3$ carbohydrates, 0.21% $C_4$ carbohydrates, and 0.12% $C_5$ carbohydrates. The formaldehyde conversion was 33.4% and the glycol aldehyde selectivity was 69.1%.

EXAMPLE 19

A reaction was carried out as described in Example 14 except that the preblended synthesis gas contained CO and $H_2$ in a 9:1 volume ratio. A sample of the reaction product withdrawn from the autoclave after 20 minutes of reaction analyzed as follows: 4.29% HCHO, 0.34% $H_2O$, 0.18% $CH_3OH$, 2.06% glycol aldehyde, 21.07% cyclohexanol, 71.59% N,N-dimethylacetamide, 0.37% $C_3$ carbohydrates, and 0.1% $C_4$ carbohydrates. The formaldehyde conversion was 27% and the glycol aldehyde selectivity was 57.4%.

It is to be noted from Examples 14 through 19 that a variation in the volume ratios of CO to $H_2$ in the reaction has a somewhat significant impact on the formaldehyde conversion but a lesser impact on glycol aldehyde selectivity. Thus, when the CO to $H_2$ volume ratio is less than 1:1 (as in Examples 14 through 16) a maximum formaldehyde conversion is obtained with no significant impact on glycol aldehyde selectivity except when the ratio approaches 1:1. However, when the CO and $H_2$ volume ratio exceeds 1:1 (as in Examples 17 through 19) a significant decrease in formaldehyde conversion is experienced, but the glycol aldehyde selectivity is not affected below acceptable levels.

The $C_3$ carbohydrates referred to in the preceding examples have been found by analysis to consist principally of glycerol, glyceraldehyde and dihydroxyacetone. The $C_4$ carbohydrates appeared to comprise erythrose, threose, and glycero-tetrulose. These analyses were carried out by gas chromatographic methods in which the reaction products were first reacted with hydroxylamine hydrochloride to form the oxime derivatives and these were then reacted with trimethylchlorosilane to form trimethylsilyl derivatives which were analyzed in a gas chromatograph. The analytical procedure used is published in the Journal of Chromatographic Science, Vol. 21, 132–138, (March, 1983).

Although the preceding examples illustrate processes in which basic organic amine compositions were employed to promote the reaction of hemi-formal (or paraformaldehyde in Examples 9, 11 and 13) with carbon monoxide and hydrogen, the processes of the present invention can be carried out in the absence of such amine compositions as illustrated in the following examples.

EXAMPLE 20

In this run the autoclave and its accessories, as described in Example 1, were used and the autoclave was pressurized with preblended synthesis gas $(CO:H_2=1:1)$ all as described in Example 1. The autoclave was charged with 0.345 grs (0.5 mmol) $RhCl(CO)[P(C_6H_5)_3]_2$, 24.5 grs. (0.188 mole) cyclohexyl hemi-formal and 71.8 grs. N,N-dimethylacetamide (solvent). The autoclave contents were heated to a temperature of 110° C. and a gas pressure (of CO and $H_2$) of 1800 psig. The reaction was allowed to proceed for one hour at such temperature and at a pressure of 2500 psig after which the reaction products and autoclave contents were analyzed. The analyses showed the following: 1.6% HcHO, 0.4% $H_2O$, 0.1% methanol and 5.4% glycol aldehyde. These analyses do not include the solvent. The formaldehyde (in the hemi-formal) conversion was 73% and the selectivity to glycol aldehyde and methanol, respectively, was 65% and 3%.

EXAMPLE 21

A reaction was carried out as described in Example 20 except that there was charged to the autoclave 0.55 grs. (0.5 mmol) of RhCl(CO)

4.2 grs. (9 mmol) of tris(p-trifluoromethylphenyl)phosphine, 24.2 grs. (o.186 mole) cyclohexyl hemi-formal and 65 grs. of N,N-dimethylacetamide (solvent). The reactor contents were heated to a temperature of 110° C. and a pressure of 1800 psig due to CO and $H_2$ gas in a mol ratio of 1:1, and the reaction was run at 110° C. and 2500 psig for 3 hours. The contents of the autoclave were analyzed and the following were found: 1.7% HCHO, 0.4% $H_2O$, 0.2% methanol and 6.7% glycol aldehyde. These analyses do not include the solvent. The formaldehyde (in the hemi-formal) conversion was 71% and the selectivity to glycol aldehyde and methanol, respectively, was 82% and 6%.

As noted previously herein, one of the important advantages of the present invention employing hemi-formals is that the hemi-formals enable the essentially complete use of the formaldehyde content thereof without loss in the overall process. This will be more evident from the following. In recovering the glycol aldehyde from the reaction mixture water is normally used to extract such aldehyde from the catalyst and other water-insolubles in the reaction mixture. If formaldehyde is used as a reactant (rather than hemi-formal) the formaldehyde is extracted into the water along with the glycol aldehyde and must be separated from such aldehyde by expensive procedures. On the other hand, when a hemi-formal is used as a reactant it is water immiscible and thus is readily separated physically by decantation or otherwise from the water used to extract glycol aldehyde, and is returned to the process for further reaction with CO and $H_2$ or used to recover HCHO from a HCHO manufacturing process. Thus the HCHO content of the hemi-formal is not lost nor does it require separation from the glycol aldehyde dissolved in the water extractant.

Those skilled in the art will recognize that certain equivalents to the materials used in the present processes may be used, and it is intended that such equivalents be included within the scope of the present invention.

What we claim is:

1. A process for the production of glycol aldehyde which comprises reacting (1) a liquid hemi-formal having the formula R'—O—$CH_2$—OH, wherein R' is an alkyl or cycloalkyl group, (2) carbon monoxide and (3) hydrogen in a solvent system and in the presence of an amount of rhodium catalyst sufficient to catalyze the formation of glycol aldehyde and wherein said catalyst has at least one modifying ligand associated with one rhodium atom and said ligand is a tertiary organo phosphine moiety or a tertiary organo arsenic moiety or combinations thereof, said process being further characterized in that it is carried out under conditions of elevated pressure and elevated temperature conducive to the formation of glycol aldehyde.

2. A process as in claim 1, wherein said hemi-formal, carbon monoxide and hydrogen are reacted in a solvent system in the presence of said catalyst and also in the presence of a basic organic amine composition having a pKa of at least 1.0 serving to improve the reaction rate and the yield of glycol aldehyde.

3. A process as in claim 2, wherein said hemi-formal has from 5–10 carbon atoms and said basic amine composition has a pH in water solution in excess of the pH in water of any reactant or solvent employed in said process.

4. A process as in claim 3, wherein said hemi-formal is cyclohexyl hemi-formal and said basic amine composition is a tertiary amine.

5. A process for the production of glycol aldehyde which comprises reacting carbon monoxide and hydrogen in a mol ratio of about 4:1 to about 1:2 with cyclohexyl hemi-formal in a solvent system under a pressure of about 200 to about 6000 psig and a temperature of about 90° to about 120° C. in the presence of (1) an amount of a rhodium catalyst sufficient to catalyze the formation of glycol aldehyde and wherein said catalyst has an amount of tertiary organo phosphine in excess of one organo phosphine ligand associated with one rhodium aton and (2) a basic organic amine compound having a $pK_a$ of about 4.0 to about 12.5 in an amount sufficient to provide about 1 to about 5 moles of said amine compound per rhodium atom in said catalyst.

6. A process as in claim 5, wherein the phosphine is triphenyl phosphine and the amount of said phosphine product exceeds 2 mols per rhodium atom.

7. A process as in claim 6, wherein the basic amine compound is a tertiary amine.

8. A process for the production and recovery of glycol aldehyde which comprises reacting (1) a liquid, water immiscible hemi-formal having the formula R'—O—$CH_2$—OH, wherein R' is an alkyl or cycloalkyl group, (2) carbon monoxide and (3) hydrogen in a solvent system and in the presence of an amount of rhodium catalyst sufficient to catalyze the formation of glycol aldehyde and wherein said catalyst has at least one modifying ligand associated with one rhodium atom and said ligand is a tertiary organo phosphine moiety or a tertiary organo moeity or combinations thereof, said process being carried out under conditions of elevated pressure and elevated temperature sufficient to form a reaction mixture containing glycol aldehyde and unreacted water immiscible hemi-formal, extracting glycol aldehyde from said reaction mixture with water and physically separating the resultant water extractant from said water immiscible hemi-formal.

9. The process of claim 8 in which the water-immiscible hemi-formal is recycled for further reaction with the carbon monoxide and hydrogen.

10. The process of claim 8 in which the hemi-formal is cyclohexyl hemi-formal and a basic organic amine is present having a pka of at least 1.0 and serving to improve the reaction rate of glycol aldehyde.

* * * * *